Figure 1:
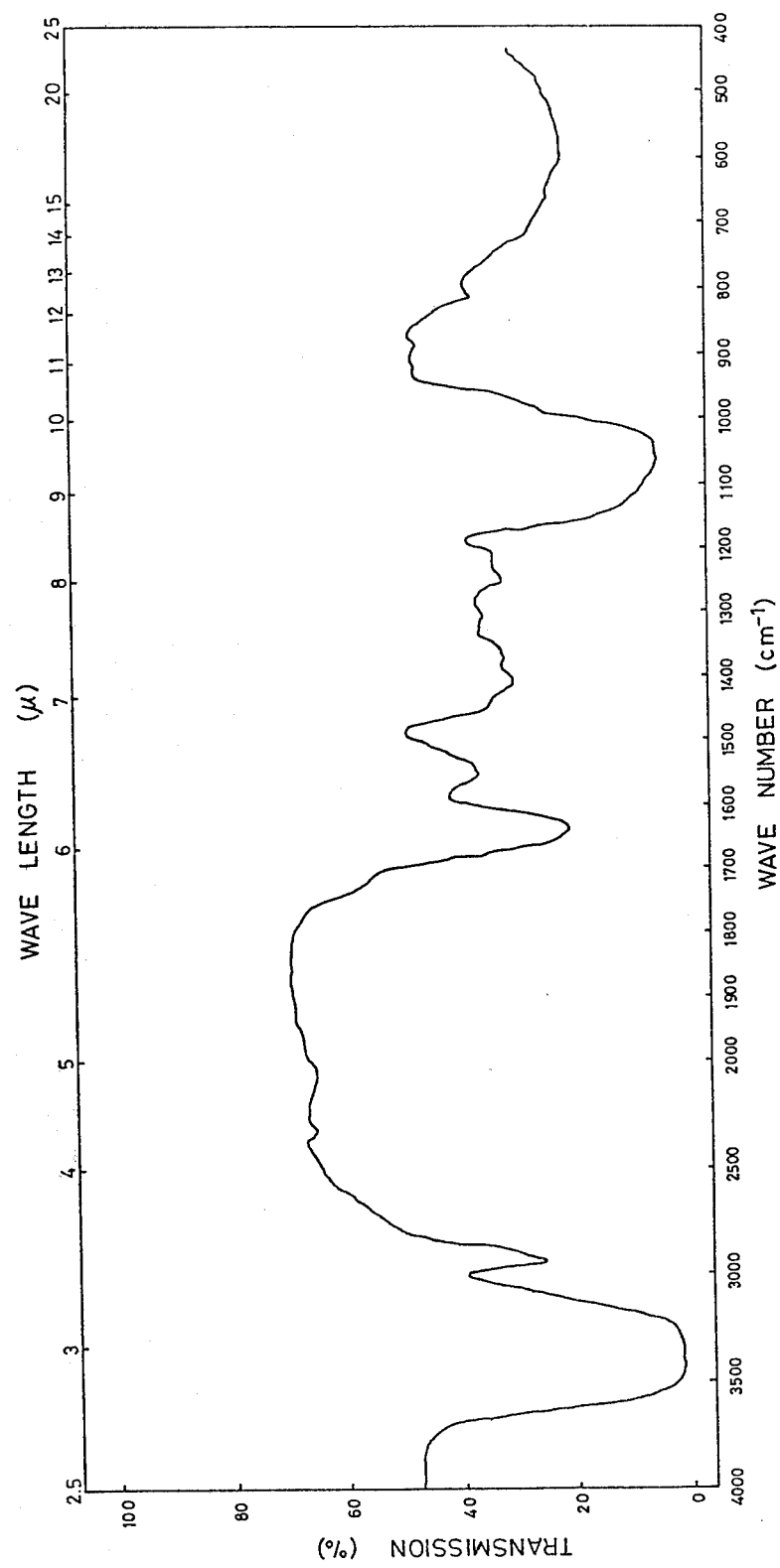

United States Patent [19]

Nakajima et al.

[11] 4,409,385

[45] Oct. 11, 1983

[54] POLYSACCHARIDES HAVING ANTICARCINOGENIC ACTIVITY AND METHOD FOR PRODUCING SAME

[75] Inventors: Kazuo Nakajima, Kyoto; Yoshiaki Hirata; Hiroyuki Uchida, both of Otsu; Yoshie Kimizuka; Tsutomu Taniguchi, both of Kyoto; Akira Obayashi; Osamu Tanabe, both of Uji, all of Japan

[73] Assignee: Takara Shuzo Co., Ltd., Kyoto, Japan

[21] Appl. No.: 231,575

[22] Filed: Feb. 3, 1981

Related U.S. Application Data

[63] Continuation-in-part of Ser. No. 175,690, Aug. 5, 1980, abandoned.

[30] Foreign Application Priority Data

Aug. 8, 1979 [JP] Japan .................................. 54-101100

[51] Int. Cl.$^3$ .......................... C07H 1/08; C08B 37/00
[52] U.S. Cl. .................................... 536/123; 424/180; 536/1.1; 536/127

[58] Field of Search ..................... 536/1, 1.1, 123, 127

[56] References Cited

U.S. PATENT DOCUMENTS

| | | | |
|---|---|---|---|
| 3,314,801 | 4/1967 | Cadmus et al. | 536/1 |
| 3,436,346 | 4/1969 | Westover et al. | 536/1 |
| 3,923,782 | 12/1975 | Finn et al. | 536/1 |
| 4,202,885 | 5/1980 | Asano et al. | 536/1 |
| 4,202,969 | 5/1980 | Ueno et al. | 536/1 |
| 4,210,641 | 7/1980 | Brossard et al. | 536/1 |
| 4,268,505 | 5/1981 | Yoshikumi et al. | 536/1 |

OTHER PUBLICATIONS

Nakajima, et al., "Chem. Abst." vol. 94, 1981, p. 172889d.

*Primary Examiner*—Johnnie R. Brown
*Attorney, Agent, or Firm*—Wenderoth, Lind & Ponack

[57] ABSTRACT

A polysaccharide having anticarcinogenic activity, and a process for its production from a strain of the genus Isaria of the class Hyphomycetes.

4 Claims, 3 Drawing Figures

POLYSACCHARIDES HAVING ANTICARCINOGENIC ACTIVITY AND METHOD FOR PRODUCING SAME

This application is a continuation-in-part of Ser. No. 175,690, filed Aug. 5, 1980, now abandoned.

This invention relates to polysaccharides having an anticarcinogenic activity and also to a process for producing them.

More particularly this invention relates to polysaccharides having an anticarcinogenic activity and to a process for producing such polysaccharides from an extract of mycelium and/or stromatoid of a strain which is capable of producing an anticarcinogenic polysaccharide and which belongs to the genus Isaria of the class Hyphomycetes or from a culture medium in which said strain has been incubated.

According to this invention there can be used any strain of species belonging to the genus Isaria of the class Hyphomycetes and which is capable of producing an anticarcinogenic polysaccharide.

However in the embodiments of this invention to be explained hereinafter there was used a strain of *Isaria atypicola Yasuda* K-2583 which was obtained by the cultivation of a stromatoid (tissue) of a fungi species collected at "Kiyotaki", Kyoto Prefecture, Japan in the summer of 1965. The identification of this species was made by using the following books; "Icones of Japanese Fungi" ed. By Seiichi Kawamura (published by Kazama-shobo, Tokyo, Japan) 8, 854–857, 1968; "Colored Illustrations of Fungi of Japan" ed. by Rokuya Imazeki and Tsugio Hongo (published by Hoiku-sha, Osaka, Japan) 1965.

Thus the characteristics of this strain are as follows. This strain is parasitic on *Kishinouyeus typicus Kishida* (a sort of spider), and the dead body of this spider is covered with mycelium of this strain under the ground and from which the stromatoid develops. The stromatoid is 5–8 cm. in height and white, cylindrical, flesh in shape. At the top of the stem which is 2.5–4.0 mm. in diameter and has the smooth surface, there is a bearing part which is slightly thick, and longer in shape than the stem. The bearing part has slight velvet-like, violet spores and these are cylindrical, semi-smooth, and colorless with a size of $4-5 \times 1.5-2.0\mu$.

From these characteristics and by referring to the above cited books this strain was identified with *Isaria atypicola Yasuda*. This strain was deposited at Fermentation Research Institute, Agency of Industrial Science and Technology, Japan under FERM-P 5086 and also at American Type Culture Collection under ATCC 20603.

The anticarcinogenic polysaccharide of this invention can be obtained from a liquid extract of stromatoid and/or mycelium of this strain which has been incubated, or from a filtered broth of the culture in which such mycelium has been incubated.

However, it is not easy to collect such stromatoid in a sufficiently large amount in natural field. Therefore, it is advantageous to incubate the strain to obtain a large amount of stromatoid. The incubation may be conducted in a manner well known for the incubation of fungi of the class Hyphomycetes, for example on wood dust or saw dust medium. Thus, for example, 200 g. of saw dust, 100 g. of rice bran and 300 ml of water are well mixed to prepare a culture medium, which is packed in a suitable vessel and sterilized. The strain which has been cultured separately in a slant culture medium is incubated on the above prepared culture medium in a conventional manner at 25°–27° C. for about one month to sufficiently grow the mycelium. The culture medium was then left to stand for about one month at 20°–25° C. so that the stromatoid grows thereon. The stromatoid so grown is collected and used as the starting material of this invention.

The mycelium to be used in this invention may be obtained by a conventional cultivation method such as solid culture or liquid culture. In solid culture, for example, agar, gelatin, starch, wood dust, pulp, other conventional solid culture medium or a combination thereof may be used. In liquid culture there may be used a liquid culture medium containing various nutrients which are well known in the art of cultivation of microorganisms. Thus the liquid culture medium may contain a carbon source such as glucose, maltose, lactose, sucrose, starch, molasses, etc., a nitrogen source (organic and inorganic nitrogen source material) such as peptone, yeast extract, yeast, corn steep liquor, urea, ammonium salts, etc., and one or more of organic and inorganic salts such as phosphates, magnesium salts, etc. If desired other material necessary for the growth such as vitamins may also be added. These materials for solid and liquid culture media are well known per se in the art of cultivation of fungus, and no further detailed explanation would be required therefor. The liquid culture may be conducted in any conventional manner such as stationary culture, shaking culture or submerged culture. For economy and ease of handling, liquid culture is more advantageous than solid culture.

In conducting the liquid culture the following conditions may be used:

| Initial pH | 2–9 |
|---|---|
| Incubation temp. | 15–35° C. |
| Incubation period | 3–30 days |

In case of submerged culture the medium is subjected to aeration at a rate of 0.1–2.0 L/L/min. with stirring at a rate of 30–500 r.p.m.

The mycelium grown by the solid or liquid culture is collected in a conventional manner and used as the starting material of this invention.

For example, in case of liquid culture, the mycelium may be collected by subjecting the resulting liquid culture medium to a conventional separation procedure such as centrifugation, filtration, etc. The filtrate obtained by this separation procedure is referred to as filtered broth, which may also be used as the starting material of this invention.

According to this invention, the stromatoid and/or mycelium collected in the above mentioned manner is subjected to extraction with an aqueous solvent. In this case the stromatoid and/or mycelium as such may be directly subjected to the extraction. If desired, prior to such extraction, the stromatoid and/or mycelium may be subjected to a pretreatment such as washing with water, air drying, crushing (pulverization) or extraction with a non-polar solvent.

The aqueous solvent to be used for the extraction is water or a mixture of water and at least one water soluble material such as acid, base, salt, or organic solvent.

In conducting the extraction the pretreated or non-pretreated stromatoid or mycelium is mixed with the aqueous solvent. The temperature of the solvent is not critical if maintained below 120° C. Preferable temperature may be chosen from an economic view point. The extraction is conducted for a period of time sufficient to effect the desired extraction. Generally, at a higher temperature the extraction time may be shorter. Within the above indicated preferred temperature range, the extraction is carried out preferably for a period of time from 30 minutes to 10 hours. The extraction is carried out preferably under agitation in a vessel which may be made of glass, glass-lined, enameled or stainless steel. The amount of the solvent may also vary over a wide range but is generally 10–100 times the weight (on dry basis) of the stromatoid and/or mycelium. The use of pulverized stromatoid or mycelium is preferable for the extraction. After the extraction the mycelium or stromatoid and other solid matter are removed from the liquid extract by any convenient means such as filtration or centrifugation. The liquid extract is concentrated, for example, by vacuum evaporation or the like for further treatment. Generally the aqueous extract is concentrated to $\frac{1}{3}$–1/10 of the initial volume.

The extract obtained as described above is then subjected to purification to be explained below, resulting in the precipitation and recovery of the intended polysaccharide. The term "liquid extract" as used herein means a filtrate or centrifugate resulting from the removal of the mycelium and/or stromatoid and other solid matters from the extract.

The filtered broth may also preferably be used for the purification to be explained below, resulting in the precipitation and recovery of the intended polysaccharide. The term "filtered broth" as used herein means a filtrate containing the active ingredient, i.e. polysaccharide, and is obtained by the removal of mycelium and other solid matters from the cultured broth, i.e. culture medium in which the strain has been incubated by liquid culture in the manner as explained before. The filtered broth is concentrated, for example, by vacuum evaporation or the like for further treatment. Generally the filtered broth is concentrated to $\frac{1}{3}$–1/10 of the initial volume. The concentrated filtered broth is then subjected to the purification.

The liquid extract and the filtered broth may be subjected to the purification separately, or the liquid extract and the filtered broth may be combined together so that the mixture is subjected to the purification.

The purification may be conducted in any of the following procedures.
(A) Precipitation of the desired substance by the addition of a highly polar organic solvent (such as lower alcohols and ketones, e.g. methanol, ethanol, propanol, butanol, acetone, etc.) or by salting out (by the addition of water-soluble inorganic salts such as ammonium sulfate, sodium chloride, potassium chloride, etc.).
(B) Removing acids, ions and low molecular weight substances by any of dialysis, gel filtration (by the use of dextran or polyacrylamide gel such as Sephadex, Bio-Gel, etc.), ion exchange resin treatment (by the use, for example, of various commercial anion and cation exchange resins such as Amberlite, Dowex, Duolite, etc.), ultrafiltration and a combination thereof, to produce a substantially pure solution from which the desired active substance is recovered.
(C) Treatment for removal of free proteins, such as Sevag method, trifluorotrichloromethane method, protease treatment, etc.

These procedures are well known per se in the art. If desired two or more of them may be combined. Generally, however, the liquid extract or filtered broth, after concentration, is subjected to a procedure selected from ion-exchange resin treatment, dialysis, gel filtration, ultrafiltration and a combination thereof to effect decoloration, deacidification, and removal of low molecular weight substances. From such purified solution the desired active substance may be removered by a proper procedure such as freeze drying. If desired the above mentioned procedure(s) may be repeated to obtain the desired extent of purification.

The substance thus obtained has the following characteristics:
(1) This substance is white or slight brown powder and non-dialyzable.
(2) Molisch reaction, Anthrone reaction and ninhydrin reaction are positive.
(3) Elson-Morgain reaction is weak positive or negative.
(4) Iodide reaction and Bial reaction are negative.
(5) This substance is soluble in water and in an aqueous solution of a substance soluble in water, e.g. organic solvent, acid, base salt and the like, but insoluble in an organic solvent such as petroleum ether, ethyl ether, benzene, acetone, ethanol, methanol, etc.
(6) This substance is without a sharp melting point and is carbonized upon strong heating.
(7) The hydrolyzate of this substance obtained by dissolving this substance in 0.1 N aq. sulfuric acid and heating the solution (containing 0.5% by weight of this substance) at 100° C. for 5 hours contains one or more of glucose, galactose and mannose, the kind(s) of the sugar varying depending upon the kind or extent of the purification.
(8) Elemental analysis of this substance is C; 35.78%, H; 6.28%, N; 0.65%.

From the above characteristics this substance is believed to be a high molecular weight polysaccharide composed of the sugar mentioned above and having a molecular weight of at least 8,000 and an average molecular weight of about $2 \times 10^5$.

The polysaccharide of this invention exhibits neither cytotoxicity nor side effects commonly seen in connection with the use of conventional agents such as decrease in number of leucocytes, anemia of liver and other organs, atorophy of the spleen, loss of body weight and loss of appetite. The acute toxicity ($LD_{50}$) of this polysaccharide in mice is more than 2000 mg/kg when intraperitoneally injected.

The polysaccharide of this invention has an anticarcinogenic activity. The anticarcinogenic activity has been confirmed and determined by the following test.

Thus, a mouse of ICR-JCL strain weighing $20 \pm 2$ g. was inoculated intraperitoneally with Sarcoma-180 cancer or Ehrlich cancer cells. After one week from the inoculation a sufficient increase of ascitic fluid was observed in the mouse. The cancer cells therein were subcutaneously transplanted at axillary area of the other mice at a rate of 4,000,000 cells per mouse. These mice were divided into several groups, each composed of five to eight mice. The first group (control group) was administered only with saline, while each of the other groups was administered with the polysaccharide of this invention. The first administration of saline or the polysaccharide was made intraperitoneally one day after transplantation, and the administration was repeated 4 times (giving a total of 5 administrations), once every other day. An observation was made of the solid cancer transplanted on mice, and the 18th day from the last administration the average increase of body weight was measured and the mice were then anatomized to check side effects and to determine the weight of tumors removed from the control group as well as those removed from the polysaccharide-treated groups. The "inhibition ratio (IR)" indicated in the following tables was calculated according to the formula:

IR(%) = (C̄−T̄)/C̄ × 100 wherein C̄ represents an average weight of the tumors removed from each of the control group mice and T̄ represents an average weight of tumors removed from the polysaccharide-treated group mice.

The anticarcinogenic activity against syngeneic tumor in the mice has also been determined. The test method was the same as described above except for the tumor, the stock of mice and administration method. The 3-methylcholanthrene-induced sarcoma (Meth A) of BALB/C origin was used in the solid form in syngeneic mice. The stock of mice used in this test were BALB/C from Charles River Breeding Laboratories in Japan. The administration method was i.t. (intratumorally). The administration was effected one time each day for 10 days.

It has been confirmed that the polysaccharide of this invention exhibits strong anticarcinogenic activity against Sarcoma-180, Ehrlich carcinoma and Meth A.

Figure 2:
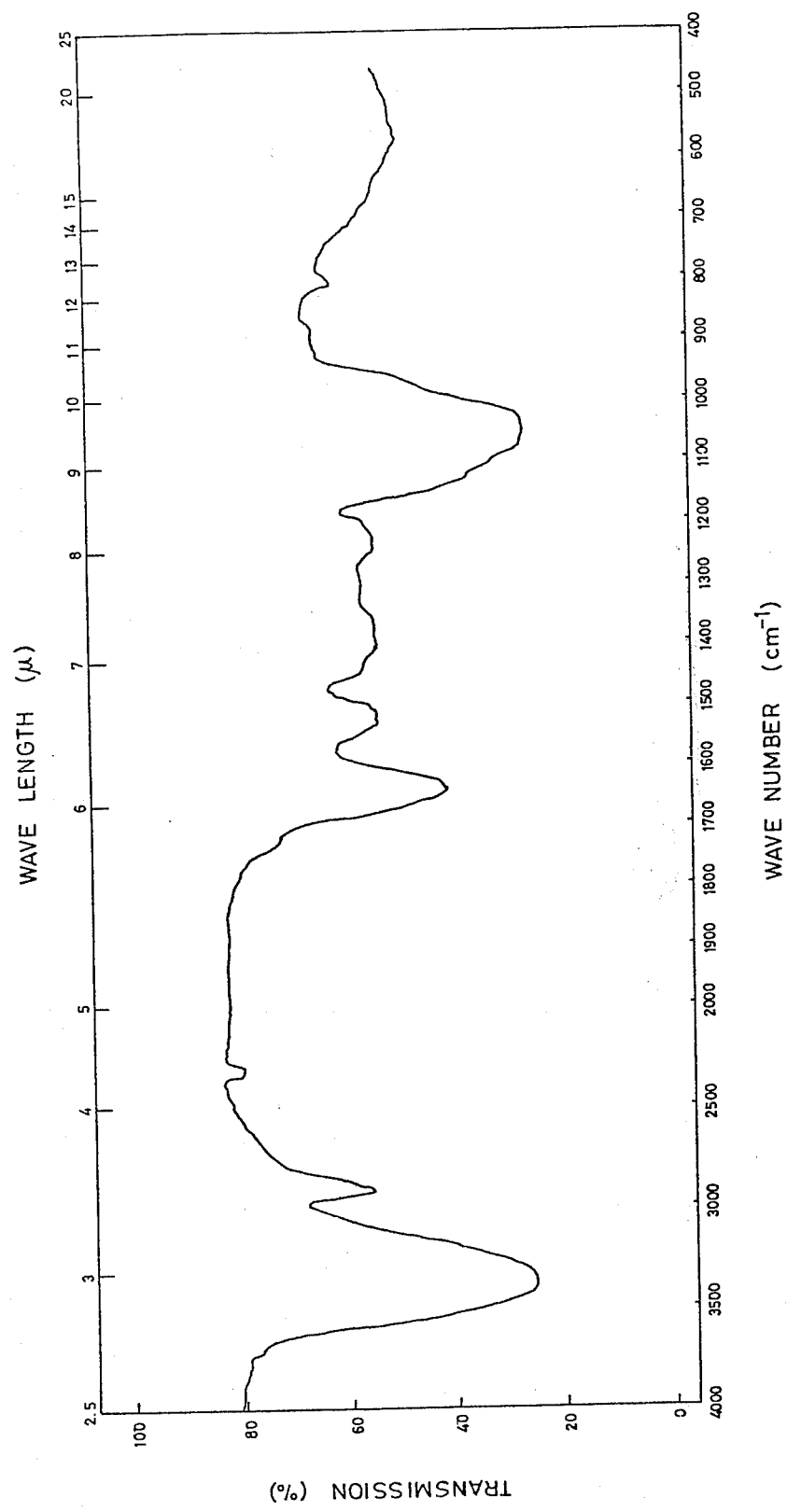
Figure 3:
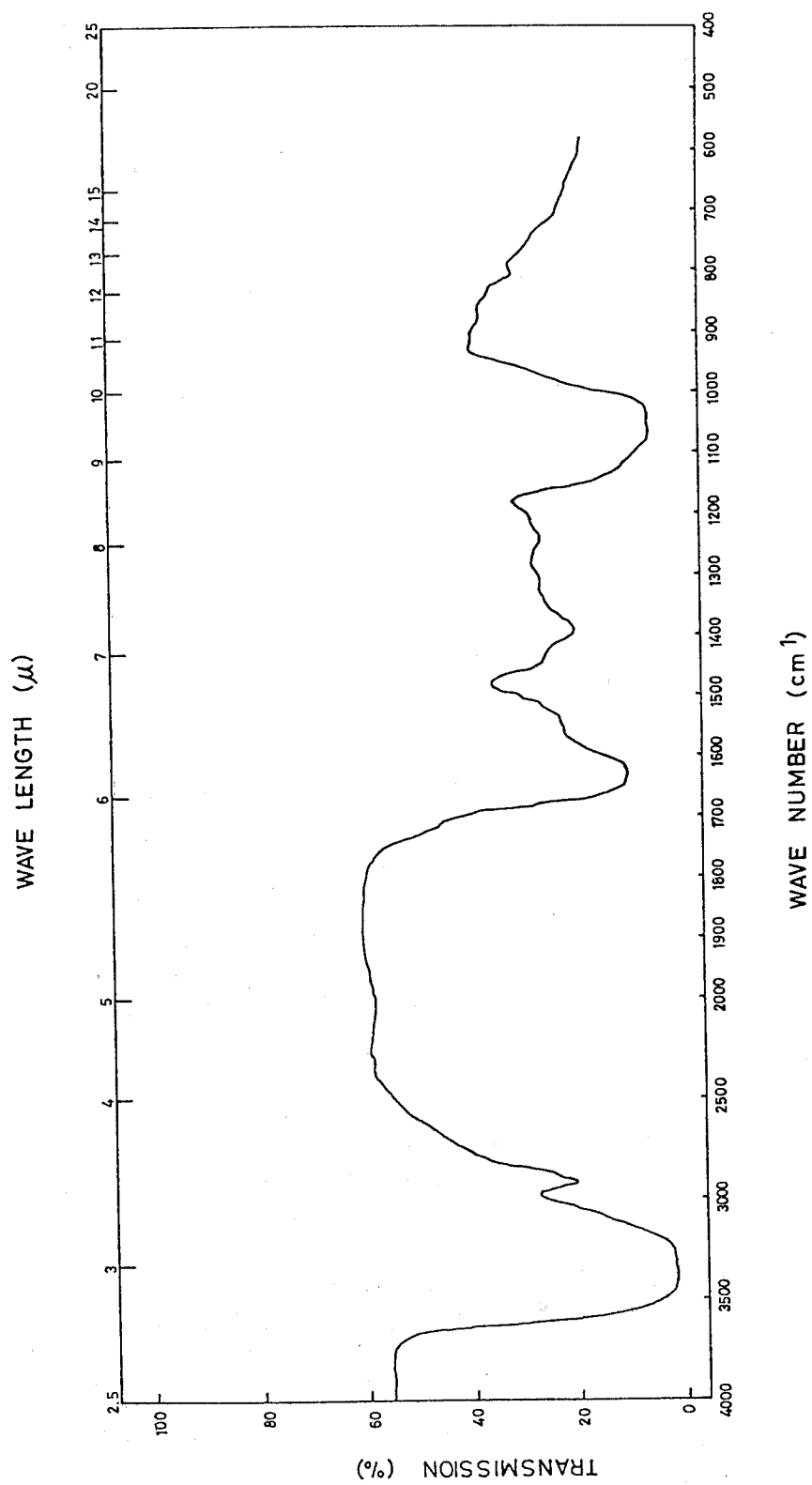

The invention will be further explained in the following Examples with reference partly to the drawings wherein FIGS. 1, 2 and 3 are infrared spectra of polysaccharides according to this invention (as KBr tablet).

EXAMPLE 1

A strain (FERM-P 5086, ATCC 20603) of *Isaria atypicola Yasuda* was incubated in the following liquid culture medium:

| | |
|---|---|
| Glucose | 20 g. |
| Polypeptone (Daigo) | 5 g. |
| Yeast extract (Difco) | 1 g. |
| Potassium phosphate (Primary) | 1 g. |
| Magnesium sulfate (7H$_2$O) | 0.5 g. |
| Water | 1 liter |
| Initial pH | 5.6–5.8 (without adjustment). |

The incubation was conducted by charging 100 ml of the above culture medium to each of 500 ml Erlenmeyer flasks. The flasks were stopped with cotton, sterilized for 30 minutes at 120° C. After cooling they were inoculated in a conventional manner with said strain which had been cultured separately in a slant culture medium containing 2% glucose, 0.5% Ebios and 1.5% agar. After 7 days shaking incubation at 27° C., the contents of the flasks were used for the subsequent incubation. Twenty liters of the liquid culture medium described above in a 30 liter stainless steel jar fermenter were sterilized at 120° C. for 30 minutes and cooled. Then, the content of the flasks obtained above was inoculated in the culture medium in said jar fermenter. The medium was subjected to aerobic incubation with stirring (250 r.p.m.) for 16 days at 27° C., and with an aeration rate of 0.5 liter/liter/minutes. The cultured broth thus obtained was filtered to yield 1700 g. of mycelium (wet) and 15 liters of filtered broth. The mycelium was washed with one liter of water and the washing liquid was combined with the filtered broth. The washed mycelium was mixed with 2 liters of water and the mixture was heated at 120° C. for 30 minutes in a closed vessel. Then the mixture was allowed to cool to room temperature and filtered, followed by concentration of the filtrate to 1 liter. The concentrated liquid extract was dialyzed with water and then freeze-dried to yield 4.0 g. of white to slight brown powdery substance. The infrared spectrum of this substance is shown in FIG. 1.

The filtered broth (16 liters) was concentrated to 2 liters and dialyzed with water and freeze-dried to yield 26.5 g. of white to slight brown powdery substance. The infrared spectrum of this substance is as shown in FIG. 2.

The anticarcinogenic activities of these polysaccharide substances were as shown in Tables 1 and 2.

TABLE 1

| Dosage mg/kg/day | Route | Complete regress. | IR % |
|---|---|---|---|
| The substance from mycelium | | | |
| 10 | ip | 2/8 | 83.8 |
| 50 | ip | 7/8 | 94.1 |
| 250 | ip | 4/8 | 79.5 |
| The substance from filtered broth | | | |
| 0.5 | ip | 0/8 | −9.8 |
| 5 | ip | 3/8 | 73.0 |
| 50 | ip | 7/8 | 96.0 |

Cancer cell: Sarcoma 180 4 × 10$^6$ cells/mouse
Animal stock: ICR-JCL 20 g. ± 2 g.
Treatment: Administered intraperitonially one day after transplantation (control: saline); 5 times.
Determination: Tumor weight of solid type.
IR (Inhibition ratio) = (C̄ − T̄)/C̄ × 100
C: Average weight of tumors removed from control group.
T: Average weight of tumors removed from the polysaccharide treated group.

TABLE 2

| Dosage mg/kg/day | Route | Complete regress. | IR % |
|---|---|---|---|
| The substance from mycelium | | | |
| 10 | ip | 2/8 | 81.5 |
| 50 | ip | 7/8 | 94.3 |
| 250 | ip | 5/8 | 80.9 |
| The substance from filtered broth | | | |
| 0.5 | ip | 0/8 | −9.7 |
| 5 | ip | 4/8 | 75.2 |
| 50 | ip | 7/8 | 96.3 |

Cancer cell: Ehrlich carcinoma 4 × 10$^6$ cells/mouse
Animal stock, Treatment and Determination were same as Table 1.

EXAMPLE 2

The strain of FERM-P 5086, ATCC 20603 was incubated in a jar fermenter in the same manner as in Example 1. Then the filtered broth (16 liters) was subjected to purification in the following manner. Thus the filtered broth was concentrated to 2 liters by vacuum evaporation and the concentrate was dialyzed for 24 hours in flowing water. The dialyzate (2.5 liters) was adjusted to pH 8.0 by aq. NaOH and subjected to DEAE-Sephadex treatment. The liquid which passed through DEAE-Sephadex was adjusted to pH 3.5 by HCl and then subjected to SP-Sephadex treatment. The liquid which passed through SP-Sephadex was mixed with ethanol to a 50% alcohol concentration to form a precipitate, which was dissolved in 1 liter of water and again subjected to dialysis in flowing water for 24 hours. The dialyzate was freeze-dried to obtain 24.9 g. of solid substance (polysaccharide), which is a white to slight brown powdery substance composed of glucose, galactose, mannose. The infrared spectrum of this substance is as shown in FIG. 3.

The anticarcinogenic activities of this substances in mice were as follows:

| (A) Anticarcinogenic activity in mice (Sarcoma-180) | |
| --- | --- |
| Cancer cell: | Sarcoma-180 $4 \times 10^6$ cells/mouse |
| Animal stock: | ICR-JCL $20 \pm 2$ g. |
| Treatment: | Administered intraperitoneally one day after transplantation (control: saline); 5 times. |
| Determination: | Tumor weight of solid type tumor IR (Inhibition ratio) = $(C - T)/C \times 100$ C: Average weight of tumors removed from control group. T: Average weight of tumors removed from the polysaccharide treated group. |
| (B) Anticarcinogenic activity in mice (Sarcoma-180) | |
| Treatment: | Administered intravenously one day after transplantation (control: saline); 5 times. |
| Cancer cell, Animal stock and Determination were same as (A). | |
| (C) Anticarcinogenic activity in mice (Meth A) | |
| Cancer cell: | Meth A $2 \times 10^4$ cells/mouse |
| Animal stock: | BALB/C 20 g. $\pm 2$ g. |
| Treatment: | Administered intratumorally every day beginning one day after transplantation (control: saline); 10 times. |
| Determination: | Same as (A). |

TABLE 3

| Dosage mg/kg/day | Route | Complete regress. | IR % |
| --- | --- | --- | --- |
| (A) | | | |
| 0.15 | ip | 2/5 | 79.0 |
| 0.80 | ip | 4/5 | 98.2 |
| 4.00 | ip | 5/5 | 100.0 |
| 20.00 | ip | 5/5 | 100.0 |
| Cont. | ip | 0/6 | — |
| (B) | | | |
| 0.02 | iv | 0/5 | −19.8 |
| 0.10 | iv | 1/5 | 46.2 |
| 0.50 | iv | 6/6 | 100.0 |
| 2.50 | iv | 6/6 | 100.0 |
| Cont. | iv | 0/7 | — |
| (C) | | | |
| 10 | it | 3/6 | 65.0 |
| 50 | it | 0/7 | 16.0 |
| Cont. | it | 0/7 | — |

What we claim is:

1. A polysaccharide isolated from a liquid extract of at least one of stromatoid and mycelium of a strain of *Isaria atypicola* of the class Hyphomycetes which is capable of producing the polysaccharide, or from a culture medium in which said strain has been incubated, said polysaccharide having anticarcinogenic activity against Sarcoma-180, Ehrlich carcinoma and Meth A, and further having the following characteristics:

(1) white or slight brown powder, non-dialyzable;
    (2) Molisch reaction, Anthrone reaction and ninhydrin reaction are positive;
    (3) Elson-Morgain reaction is weak positive or negative;
    (4) iodide reaction and Bial reaction are negative;
    (5) soluble in water and in an aqueous solution of a substance soluble in water, but insoluble in an organic solvent;
    (6) no sharp melting point, and is carbonized upon strong heating;
    (7) the hydrolyzate of the polysaccharide, obtained by dissolving the polysaccharide in 0.1 N aq. sulfuric acid and heating the solution, containing 0.5% by weight of the polysaccharide, at 100° C. for 5 hours, contains one or more of glucose, galactose and mannose;
    (8) elemental analysis is C 35.78%, H 6.28%, N 0.65%.

2. A polysaccharide according to claim 1 wherein the strain is *Isaria atypicola Yasuda* (FERM-P 5086, ATCC 20603).

3. A process for producing a polysaccharide, which comprises forming a filtered broth from a culture medium or liquid extract of at least one of stromatoid and mycelium of *Isaria atypicola Yasuda* (FERM-P 5086, ATCC 20603) of the class Hyphomycetes which is capable of producing the polysaccharide, and recovering the polysaccharide from the filtered broth or liquid extract in a purified form, said polysaccharide having the following characteristics:

(1) white or slight brown powder, non-dialyzable;
    (2) Molisch reaction, Anthrone reaction and ninhydrin reaction are positive;
    (3) Elson-Morgain reaction is weak positive or negative;
    (4) iodide reaction and Bial reaction are negative;
    (5) soluble in water and in an aqueous solution of a substance soluble in water, but insoluble in an organic solvent;
    (6) no sharp melting point, and is carbonized upon strong heating;
    (7) the hydrolyzate of the polysaccharide, obtained by dissolving the polysaccharide in 0.1 N aq. sulfuric acid and heating the solution, containing 0.5% by weight of the polysaccharide, at 100° C. for 5 hours, contains one or more of glucose, galactose and mannose;
    (8) elemental analysis is C 35.78%, H 6.28%, N 0.65%.

4. A process according to claim 3, wherein the polysaccharide has anticarcinogenic activity against at least one member selected from the group consisting of Sarcoma-180, Ehrlich carcinoma and Meth A.

* * * * *